United States Patent [19]

Orth et al.

[11] Patent Number: 4,529,800

[45] Date of Patent: Jul. 16, 1985

[54] PROCESS FOR THE PREPARATION OF 2-HALO-3-NITRO-6-ALKOXY-PYRIDINES

[75] Inventors: Winfried Orth, Hassloch; Werner Fickert, Mannheim, both of Fed. Rep. of Germany

[73] Assignee: Rutgerswerke Aktiengesellschaft, Fed. Rep. of Germany

[21] Appl. No.: 512,652

[22] Filed: Jul. 11, 1983

[30] Foreign Application Priority Data

Aug. 19, 1982 [DE] Fed. Rep. of Germany ....... 3230828
Mar. 10, 1983 [DE] Fed. Rep. of Germany ....... 3308449

[51] Int. Cl.$^3$ .................... C07D 213/61; C07D 213/64
[52] U.S. Cl. .................................................... 546/297
[58] Field of Search ........................................ 546/297

[56] References Cited

U.S. PATENT DOCUMENTS 3,547,935 12/1970 Diehl et al. ......................... 546/297

Primary Examiner—Alan L. Rotman
Attorney, Agent, or Firm—Charles A. Muserlian

[57] ABSTRACT

A novel simple process for the preparation of 2-halo-3-nitro-6-alkoxy-pyridines having 1 to 6 alkoxy carbon atoms of high purity comprising adding 2-halo-6-alkoxy-pyridine in portions at 0° to 40° C. to a mixture of concentrated sulfuric acid and concentrated nitric acid to obtain impure 2-halo-3-nitro-6-alkoxy-pyridine, treating the latter with a solution of an alkaline reacting compound in a protic solvent and recovering the said pyridine in substantially pure form which are important intermediates for analgesics.

6 Claims, No Drawings

PROCESS FOR THE PREPARATION OF 2-HALO-3-NITRO-6-ALKOXY-PYRIDINES

STATE OF THE ART

Since 2-chloro-3-nitro-6-alkoxy-pyridines are pharmaceutical intermediates, they should be prepared with a high degree of purity. The usual manner of producing the said compounds is by nitration of 2-chloro-6-alkoxy-pyridines with nitric acid and the resulting product has to be purified before further processing. The known purification procedures involve crystallization from mixtures of solvents which has not been satisfactory since the undesired contaminants are difficult to separate and many crystallizations are required which causes not only an enormous amount of work and energy but also large reductions in yield to about 50 to 55% of the theoretical yield. The products remaining in the mother liquors are not possible to recover by further separation and the selection of several different solvent systems did not improve this method of purification.

OBJECTS OF THE INVENTION

It is an object of the invention to provide a simple process for preparation of 2-chloro-3-nitro-6-alkoxy-pyridines in high yields and with high purity.

This and other objects and advantages of the invention will become obvious from the following detailed description.

THE INVENTION

The novel process of the invention for the preparation of 2-halo-3-nitro-6-alkoxy-pyridines having 1 to 6 alkoxy carbon atoms of high purity comprises adding 2-halo-6-alkoxy-pyridine in portions at 0° to 40° C. to a mixture of concentrated sulfuric acid and concentrated nitric acid to obtain impure 2-halo-3-nitro-6-alkoxy-pyridine, treating the latter with a solution of an alkaline reacting compound in a protic solvent and recovering the said pyridine in substantially pure form. The preferred halogen is chlorine.

It was found that the solution of this problem basically depended on the process for the nitration of the 2-chloro-6-alkoxy-pyridines which has critical effects on the yield, purity and possibility of purification of the nitrated products. If the nitration is of the type normally used for the nitration of organic products, i.e., addition of a mixture of sulfuric acid and nitric acid to the 2-chloro-6-alkoxy-pyridine in a mixing tank, 2-chloro-6-alkoxy-5-nitro-pyridines are formed as the main by-product and these isomers can be separated from the respective main product only with great difficulties. It is surprising that almost no 2-chloro-6-alkoxy-5-nitro-pyridines are found in the nitration performed according to the invention during which the 2-chloro-6-alkoxy-pyridines are added in portions to the sulfuric acid and nitric acid mixture in the reaction.

It was also found that all contaminants of the crude products obtained by the nitration of 2-chloro-6-alkoxy-pyridines can be removed by a simple method when the crude products are treated with agitation for several hours with a solution of an alkaline reacting compound in a protic solvent at room temperature to moderately elevated temperature. This treatment can be carried out either by digesting the isolated, nitrated crude product for several hours in an alkaline solution followed by filtration, washing with distilled water and drying, or by dissolving the nitrated crude product in an inert water-immiscible organic solvent such as toluene or xylene, bringing this solution in contact with an aqueous alkaline solution for several hours by intensive mixing and then separating it. The purified 2-chloro-6-alkoxy-3-nitro-pyridine may be isolated by removing the solvent by distillation. This isolation can also be achieved by precipitating the purified product from the solution; which may be already evaporated, if possible, with the use of another solvent such as hexane, for example. These procedural steps make the simple preparation of 2-chloro-6-alkoxy-3-nitro-pyridines with a high purity and in good yields possible. The continuous operation is another advantage of this process.

Examples of suitable 2-chloro-6-alkoxy-pyridine starting materials are preferably those with alkyl of 1 to 4 carbon atoms such as 2-chloro-6-methoxy-pyridine, 2-chloro-6-ethoxy-pyridine, 2-chloro-6-propoxy-pyridine, 2-chloro-6-isopropoxy-pyridine, 2-chloro-6-n-butoxy-pyridine and 2chloro-6-isobutoxy-pyridine.

In a preferred embodiment of the invention, the 2-chloro-6-alkoxy-pyridine is metered into the nitrating mixture of sulfuric acid and nitric acid at 0° to 40° C. and after recovering the nitrated product from the reaction mixture, treating the latter with the alkaline reacting compound. It is obvious that the treatment time is inversely proportional to the alkalinity of the solution and to the treatment temperature. For example, a brief treatment with solutions cooled to as low as 0° C. is successful when using strongly alkaline alkali metal alcoholates and digestion with cooled, aqueous alkaline solution is also be possible, but is not economically feasible because of the long treatment time. On the other hand, decomposition reactions of the 2-chloro-6-alkoxy-3-nitro-pyridines in the alkaline medium can be expected at temperatures above 50° C. which take place more readily, the stronger the alkalinity of the medium.

Examples of suitable protic solvents are water and other solvents capable of releasing protons like alkanols such as methanol and ethanol. Examples of suitable alkaline reacting compounds are alkali metal oxides and alkali metal hydroxides, ammonium hydroxide, alkaline acting salts when hydrolyzed such as alkali metal carbonates, trialkali metal phosphates, water-soluble organic amino compounds such as methylamine, dimethylamine, trimethylamine, ethylamine, ethanolamine and pyridine.

The alkaline solution shall be used in such an amount so that the resulting slurry is easy to handle, i.e., that the contact possibilities between the reaction partners are adequate and the amount of alkali used should be at least equivalent to the expected amount of contaminants. On the other hand, working with an excess of alkali offers the advantage of carrying out the purification quantitatively within the shortest time possible.

In the following examples there are described several preferred embodiments to illustrate the invention. However, it is to be understood that the invention is not intended to be limited to the specific embodiments.

EXAMPLE 1

143.6 g (one mole) of 2-chloro-6-methoxy-pyridine were added dropwise with stirring over one hour to a mixture of 1600 ml of concentrated sulfuric acid and 800 ml of fuming nitric acid cooled to 0° C. and the temperature was allowed to rise to 20° C. over three hours. The mixture was then stirred at 20° C. for three hours and was poured into 5000 g of crushed ice. The mixture was vacuum filtered and the product was washed with a large volume of water until acid free and dried to obtain 151–156 g (80–83% yield) of 2-chloro-3nitro-6-methoxy-pyridine in the form of yellow crystals melting at 67° to 69° C. with a purity of 84 to 85%.

EXAMPLE 2

A mixture of 3,300 g of impure, powdered 2-methoxy-3-nitro-6-methoxy-pyridine obtained by Example 1, 6,600 ml of water and 910 g of potassium carbonate was stirred for two hours at 40° C. and was then vacuum filtered. The product was washed with 4000 ml of water and dried at 40° to 45° C. to obtain 2,772 to 2,805 g of 2-chloro-3-nitro-6-methoxy-pyridine melting at 179° C. with a purity of 99 to 100%.

EXAMPLE 3

157.6 g (1 mole) of 2-chloro-6-ethoxy-pyridine were slowly added over 45 minutes with stirring to a mixture of 190 ml of concentrated sulfuric acid, 190 ml of 24% oleum and 100 ml of 97% nitric acid while keeping the reaction temperature between 20° and 40° C. with cooling and the mixture was allowed to stand for 5 hours while the temperature returned to room temperature. The mixture was cooled to 0° C. and filtered with a glass frit filter. The solid product was suspended in a mixture of 100 g of potassium carbonate and 250 ml of water and the suspension was stirred for 3 hours at 30° C. and was vacuum filtered. The product was washed with water and dried at 40° C. to obtain 192 g (93% yield) of 2-chloro-3-nitro-6-ethoxy-pyridine with a purity of 98%.

EXAMPLE 4

A mixture of 500 g of 2-chloro-3-nitro-6-methoxy of Example 1 with a purity of 84 to 85% in 1500 ml of toluene and 500 ml of 24% ammonium hydroxide solution was vigorously stirred at 40° C. for 12 hours and was vacuum filtered. The decanted organic phase was distilled at 90° C. under reduced pressure to remove the toluene and the residue was added with stirring to 1000 ml of heptane. The mixture was cooled and was vacuum filtered. The recovered crystals were dried at 40° to 45° C. to obtain 345 g of 2-chloro-3-nitro-6-methoxy-pyridine melting at 79° C. with a purity of 99–100%. Another 47 g of product melting at 78°–Λ° C. were recovered by evaporating the organic mother liquors to dryness and throughly mixing the residue with heptane for a total yield of 92%.

EXAMPLE 5

A solution of 500 g of 84 to 85% pure 2-chloro-3-nitro-6-methoxy-pyridine obtained by the process of Example 1 in 1500 ml of toluene was stirred at 0° to 5° C. for 10 hours with a solution of 124 g of methylamine in 600 ml of 50% aqueous methanol and was then filtered. The decanted organic phase was treated by the procedure of Example 4 to obtain a 90 to 93% yield of pure 2-chloro-3-nitro-6-methoxy-pyridine.

Various modifications of the process of the invention may be made without departing from the spirit or scope thereof and it is to be understood that the invention is intended to be limited only as defined in the appended claims.

What we claim is:

1. A process for the preparation of 2-halo-3-nitro-6-alkoxy-pyridines having 1 to 6 alkoxy carbon atoms of high purity comprising adding 2-halo-6-alkoxy-pyridine in portions at 0° to 40° C. to a mixture of concentrated sulfuric acid and concentrated nitric acid to obtain impure 2-halo-3-nitro-6-alkoxy-pyridine, recovering the latter from the acid reaction mixture and treating the latter solid product at 0° to 50° C. with an aqueous solution of an alkaline reacting compound and recovering the said pyridine in substantially pure form by filtration, washing and drying.

2. The process of claim 1 wherein the solution is aqueous ammonium hydroxide.

3. The process of claim 1 wherein the solution is aqueous alkali metal carbonate.

4. A process for the preparation of high purity 2-halo-3-nitro-6-alkoxy-pyridines having 1 to 6 alkoxy carbon atoms comprising adding 2-halo-6-alkoxy-pyridine in portions at 0° to 40° C. to a mixture of concentrated sulfuric acid and concentrated nitric acid to obtain impure 2-halo-3-nitro-6-alkoxy-pyridine, dissolving the impure product in an inert, water-immiscible organic solvent, vigorously stirring at 0° to 50° C. a mixture of the resulting organic solution with an aqueous alkaline solution and recovering the pure product by filtration, washing and drying.

5. The process of claim 1 wherein the solution is aqueous ammonium hydroxide.

6. The process of claim 1 wherein the solution is aqueous alkali metal carbonate.

* * * * *